United States Patent
Manri et al.

(12) 
(10) Patent No.: US 10,203,277 B2
(45) Date of Patent: Feb. 12, 2019

(54) AUTOMATIC ANALYSIS DEVICE AND AUTOMATIC ANALYSIS METHOD

(75) Inventors: Chihiro Manri, Kawagoe (JP); Satoshi Mitsuyama, Tokyo (JP); Tomonori Mimura, Kasama (JP); Kumiko Kamihara, Mito (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 661 days.

(21) Appl. No.: 13/641,881

(22) PCT Filed: Apr. 5, 2011

(86) PCT No.: PCT/JP2011/058595
§ 371 (c)(1),
(2), (4) Date: Oct. 18, 2012

(87) PCT Pub. No.: WO2011/132525
PCT Pub. Date: Oct. 27, 2011

(65) Prior Publication Data
US 2013/0046480 A1  Feb. 21, 2013

(30) Foreign Application Priority Data
Apr. 20, 2010  (JP) .................. 2010-096770

(51) Int. Cl.
*G01N 21/27* (2006.01)
*G01N 35/00* (2006.01)
*G01N 21/78* (2006.01)

(52) U.S. Cl.
CPC ........... *G01N 21/272* (2013.01); *G01N 21/78* (2013.01); *G01N 35/00584* (2013.01); *G01N 35/00693* (2013.01); *G01N 2035/00465* (2013.01)

(58) Field of Classification Search
CPC .................................................. G01N 21/272
USPC ......................................................... 702/23
See application file for complete search history.

(56) References Cited

U.S. PATENT DOCUMENTS

| | | |
|---|---|---|
| 4,472,505 A | 9/1984 | Manabe et al. |
| 4,750,133 A | 6/1988 | Eiskamp et al. |
| 2009/0222213 A1 | 9/2009 | Hamazumi et al. |

FOREIGN PATENT DOCUMENTS

| | | |
|---|---|---|
| CN | 101520461 A | 9/2009 |
| EP | 2 096 442 A2 | 9/2009 |
| JP | 61-149848 | 7/1986 |
| JP | 64-68642 | 3/1989 |
| JP | 6-194313 | 7/1994 |
| JP | 10-111248 | 4/1998 |
| JP | 10-185687 | 7/1998 |
| JP | 2006-337125 | 12/2006 |
| JP | 2009-98029 | 5/2009 |

OTHER PUBLICATIONS

Chinese Office Action dated Jul. 29, 2014 for Application No. 201180019415.8.
International Preliminary Report on Patentability and Written Opinion of the International Searching Authority; International Application No. PCT/JP2011/058595; International Filing date: Apr. 5, 2011.
International Search Report; International Application No. PCT/JP2011/058595, filed Apr. 5, 2011.
K. Kanbara et al., Data Evaluation of Rate Method using Reaction Curve Approximation Method, Japanese Journal of Clinical Laboratory Automation, Sep. 1, 2009, p. 476, vol. 34, No. 4.
Y. Yamamoto, Detection of the Abnormality that Originates from Reaction System that used the Reaction Time Course, Japanese Journal of Clinical Laboratory Automation, Apr. 1, 2009, pp. 163-169, vol. 34, No. 2.
Supplementary European Search Report; International Application No. 11771862.7-1554/2562547 PCT/JP2011/058595; dated May 9, 2014.
Japanese Office Action dated May 7, 2014 for Application No. 2010-096770.

*Primary Examiner* — Jerry Lin
(74) *Attorney, Agent, or Firm* — Baker Botts L.L.P.

(57) ABSTRACT

There is provided a technique for automatically determining or predicting a line range specific to a sample that appears in a reaction curve in an automated analyzer for mixing a specimen and a reagent and measuring a change in a mixture of the specimen and the reagent with time. This invention approximates reaction curve data by a function and automatically determines a curve part at an early stage or a second stage of a reaction. The invention determines a line range not including a curve part for each sample and calculates a laboratory test value using absorbance data within the determined line range. This invention also automatically determines a start time of line at the early stage of the reaction on the basis of absorbance data obtained up to a point halfway through the reaction curve, predicts a line range on the basis of the end time of line and a planned end time of line, and calculates a predictive value on the basis of a result of the prediction.

12 Claims, 13 Drawing Sheets

(a)

(b)

| Examination item | Reagent | Approximation formula |
|---|---|---|
| Item A | Reagent a | Expression 2 |
| Item A | Reagent b | Expression 3 |
| Item B | Reagent c | Expression 4 |
| Item B | Reagent d | Expression 5 |
| : | : | : |

| Sample ID | Laboratory test value | Approximation formula | Start time of line | End time of line | Number of absorbance data in line | First index of precision | Second index of precision | ... |
|---|---|---|---|---|---|---|---|---|
| 1 | val1 | Expression 2 | $Tl1$ | $Te1$ | P1 | CV1 | Ave1±C1 | ... |
| 2 | val2 | Expression 3 | $Tl2$ | $Te2$ | P2 | CV2 | Ave2±C2 | ... |
| ⋮ | ⋮ | ... | ⋮ | ⋮ | ⋮ | ⋮ |  | ... |

| Sample ID (900) | Approximation formula (905) | Predictive value (1605) | Start time of predicted line (1620) | End time of predicted line (1630) | Number of absorbance data in predicted line (1640) | First predicted index of precision (1650) | Second predicted index of precision (1660) | Third predicted index of precision (1670) | Laboratory test value (910) | Start time of line (920) | End time of line (930) | Number of absorbance data in line (940) | First index of precision (950) | Second index of precision (960) | ... |
|---|---|---|---|---|---|---|---|---|---|---|---|---|---|---|---|
| 1 | Expression 2 | Val'1 | Tl'1 | Te'1 | P'1 | CV'1 | Ave'1 ±C'1 | Cor1% | — | — | — | — | — | — | ... |
| 2 | Expression 3 | — | — | — | — | — | — | — | val2 | Tl2 | Te2 | P2 | CV2 | Ave2 ±C2 | ... |
| 3 | Expression 1 | Val'3 | Tl'3 | Te'3 | P'3 | CV'3 | Ave'3 ±C'3 | Cor2% | val3 | Tl3 | Te3 | P3 | CV3 | Ave3 ±C3 | ... |
| .. | ... | .. | .. | .. | .. | .. | .. | .. | .. | .. | .. | .. | .. | .. | ... |

AUTOMATIC ANALYSIS DEVICE AND AUTOMATIC ANALYSIS METHOD

RELATED APPLICATIONS

This application is a U.S. national phase application under 35 U.S.C. § 371 of International Application No. PCT/JP2011/058595 filed Apr. 5, 2011claiming priority of Japanese Application No. 2010-096770 filed Apr. 20, 2010.

TECHNICAL FIELD

The present invention relates to an automated analyzer and method for performing qualitative or quantitative analysis of a biological sample such as blood or urine and, for example, to an automated analyzer and method having a function of monitoring a reaction at the time of clinical laboratory test.

BACKGROUND ART

An automated analyzer for clinical laboratory test dispenses fixed amounts of a specimen and a reagent to cause a reaction, measures the absorbance of a reaction solution for a fixed period of time, and obtains a laboratory test value (the concentration or activity value) of a substance to be measured and the like on the basis of a measurement result.

A rate method that is one of measurement methods for clinical laboratory test is mainly used to measure the activity value of an enzyme component contained in a specimen. The measurement method includes adding a fixed amount of a substrate as a reagent and measuring an element that changes when an enzyme consumes the substrate. Generally, a reagent contains a sufficient amount of a substrate. For this reason, if a reaction between a specimen and a reagent is normally being carried out, the reaction is generally such that absorbance changes linearly with time in increments of a fixed amount. In the rate method, the activity value of a substrate to be measured is obtained from the slope of such a straight line (reaction rate).

However, there may be a curve part called a lag phase before a reaction rate becomes constant (linear) due to factors such as a measurement item, the concentration of a sample, stirring status, and reaction temperature. In the case of, e.g., a high-activity sample, a reaction may progress fast. In this case, the amount of a substrate in a reagent may become insufficient during measurement, and a reaction rate in a second half may be inconstant. That is, the reaction rate in the second half may change non-linearly (in a curved manner).

As described above, a curve part may appear in reaction curve data at the beginning and at a later part of a reaction. For this reason, a conventional device adopts a process of setting a time range used for laboratory test value conversion and an absorbance limit value (Abs limit) for each item. Some of conventional devices have a function for checking linearity called a linearity check. In a linearity check, the difference between amounts of change in absorbance in a first half and a second half of a fixed photometric range is calculated, and change in absorbance is determined to be not linear if the difference is above a designated linearity check value. If the change in absorbance is determined to be not linear, a conventional device makes a notification of "abnormality."

Methods for determining a time range (line range) used for laboratory test value conversion include the methods disclosed in Patent Literatures 1 and 2. Patent Literature 1 discloses a process of calculating an absorbance difference between each pair of adjacent photometric points, setting as a reference point a range between one having the largest absorbance difference (dmax) among the pairs, and determining as a line range sections having absorbance differences that are not less than 80% of the absorbance difference (dmax) of the reference point among sections within a measurement range straddling the reference point. Patent Literature 2 discloses a process of setting the width of a range used for conversion to a fixed width, calculating a coefficient of correlation among absorbance corresponding to the range by the least squares method while shifting the range by one point at a time, starting from a top photometric point, and determining a range with the best correlation as a line range.

In recent years, there has been a need to report a result of measuring patient samples as soon as possible in the field of clinical laboratory testing in hospitals. The reaction time period during measurement of an automated analyzer is about 10 minutes. However, simply shortening a measurement time period prevents acquisition of precise results. For example, if measurement is ended at a time when a reaction is incomplete, and a laboratory test value is measured from the absorbance at the time, a precise result is not obtained. To cope with this, it is conceivable to predict the absorbance at the end of a reaction and convert the absorbance to a laboratory test value. As a method for predicting the absorbance at the end of a reaction, Patent Literature 3 is publicly known. A process of approximating reaction curve data using an approximation formula indicated by (Expression 1) and obtaining, in the case of a rate method, the slope of a straight line from two predetermined points or one predetermined point after differentiation of the approximation formula with respect to time is disclosed in Patent Literature 3. Note that, in (Expression 1), t represents a time, y represents absorbance, and that A, B, and K are parameters.

$$y = A + (B-A)/e^{Kt} \quad \text{(Expression 1)}$$

CITATION LIST

Patent Literature

Patent Literature 1: JP Patent Publication (Kokai) No. 64-68642 A (1989)
Patent Literature 2: JP Patent Publication (Kokai) No. 10-185687 A (1998)
Patent Literature 3: JP Patent Publication (Kokai) No. 6-194313 A (1994)

SUMMARY OF INVENTION

Technical Problem

Examples of reaction curve data after a main reagent is added according to a rate method are shown in FIGS. 2(a) and 2(b). A horizontal axis 110 indicates a lapse of time while a vertical axis 120 indicates absorbance. As described above, a conventional device sets a time range (line range) for each examination item, i.e., sets a start time of line and an end time of line in advance. A range 160 in FIGS. 2(a) and 2(b) indicates a time range set in advance for a given examination item.

Reference numerals 130, 140, and 150 in FIG. 2(a) denote absorbance data of different samples for a single item, and ranges 135, 145, and 155 denote respective lag phases of the absorbance data. Note that reference numeral 170 denotes a predetermined absorbance limit value.

There are some cases like the case of the absorbance data denoted by reference numeral 140 where only a part originally expected as a linear part (an object originally to be examined) is included in the predetermined time range 160. There are other cases like the case of the absorbance data denoted by reference numeral 150 where a part of the lag phase 155 is included in the predetermined time range 160.

In the case of the absorbance data denoted by reference numeral 150, reaction curve data is determined by a linearity check function of a conventional device to have an abnormality, and a corresponding sample is targeted for a reexamination. However, even in the case of the absorbance data denoted by reference numeral 150, if a linear part can be precisely determined, a reexamination is unnecessary. In a case like the case of the absorbance data denoted by reference numeral 150 where there is not much difference in linearity between the linear part and the lag phase 155, it may be impossible to detect an abnormality (that the lag phase 155 is included in a line range measurement period) in a linearity check, and the slope of the straight line may be calculated so as to include information on a curve part. In this case, the slope of a straight line is not calculated with high precision, and an error in a laboratory test value may be large.

In the case of the absorbance data denoted by reference numeral 130, a measurement result within the predetermined range 160 constitutes a straight line. The absorbance data denoted by reference numeral 130, however, exceeds the absorbance limit value in a second half of the range 160. The sample corresponding to the absorbance data denoted by reference numeral 130 is also targeted for a reexamination. However, if the absorbance of a sample concerned can be guaranteed to change linearly after the absorbance exceeds an absorbance limit value, data above the absorbance limit value can also be used for laboratory test value conversion, and reexaminations can be reduced.

Reference numeral 180 shown in FIG. 2(*b*) also denotes absorbance data related to a given examination item of a given sample. In the case of the sample, a curve part appears in a second half of the range 160. Accordingly, the sample is also classified as a reexamination target by a linearity check function of a conventional device. Even in the case of the sample, if only a part within a line range of the absorbance data denoted by reference numeral 180 can be extracted, the part can be converted to a laboratory test value, and reexaminations can be reduced.

Note that if the linearity check function of Patent Literature 1 is applied to the absorbance data denoted by reference numeral 150, photometric points exhibiting a largest absorbance difference correspond to a time surrounded by the circle in FIG. 2(*a*). However, the time is located at the boundary between the lag phase 155 and the linear part. The linearity check function of Patent Literature 1 sets the photometric points surrounded by the circle as a reference and sets a period straddling the photometric points as a line range. This means that the lag phase 155 that is not a part originally expected as a linear part is used for laboratory test value conversion. That is, an error in a laboratory test value may be large.

In the case of the linearity check function of Patent Literature 2, since the width of a range used for conversion is constant, if the range width is set to be long, a range that does not correspond to a linear part may be used for laboratory test value conversion. This may also increase an error in a laboratory test value. On the other hand, if the range width is set to be short, the number of absorbance data used to calculate a laboratory test value is small, which may also increase an error.

Similarly, in the case of Patent Literature 3 that predicts the absorbance at the end of a reaction, the slope of a straight line of reaction curve data is calculated for a predetermined range (given by a start time and an end time). Accordingly, if the predetermined range falls outside a line range of actually measured data, a precise predicted value may not be obtained.

Solution to Problem

Under the circumstances, the present invention presents an automated analyzer for mixing a specimen and a reagent and measuring a change in a mixture of the specimen and the reagent with time, including (a) a measurement point data acquisition unit which acquires a plurality of measurement point data from a reaction curve of the specimen and the reagent, (b) a data processing unit which processes the measurement point data, (c) a storage unit which stores a first approximation formula used by the data processing unit, and (d) an output unit which outputs a processing result from the data processing unit. The data processing unit executes a process of causing the first approximation formula stored in the storage unit to approximate the plurality of measurement point data and a process of determining a line range of the reaction curve on the basis of a second approximation formula that is obtained as a result of the approximation process.

Note that the data processing unit desirably has a function of calculating the second approximation formula using ones of the plurality of measurement point data which are acquired up to a predetermined time and estimating or predicting the line range of the reaction curve on the basis of the second approximation formula.

The present invention also presents an automated analysis method for measuring a change in a mixture of a specimen and a reagent with time using an automated analyzer, including (a) a process of acquiring a plurality of measurement point data from a reaction curve of the specimen and the reagent by the automated analyzer, (b) a process of causing a first approximation formula read out from a storage unit to approximate the plurality of measurement point data by the automated analyzer, and (c) a process of determining a line range of the reaction curve on the basis of a second approximation formula that is obtained as a result of the approximation process by the automated analyzer. The method also desirably includes a process of calculating the second approximation formula using ones of the plurality of measurement point data which are acquired up to a predetermined time and estimating or predicting the line range of the reaction curve on the basis of the second approximation formula.

Note that the present invention desirably has a function of calculating an index of precision for the line range and outputting the index of precision as a processing result to the output unit.

Advantageous Effects of Invention

The present invention allows setting of a line range used for laboratory test value conversion for each sample. This results in acquisition of a precise laboratory test value for each sample. The present invention also allows the number of samples targeted for reexamination to be made smaller than by conventional devices. Additionally, if a second approximation formula is calculated using a plurality of measurement point data acquired up to a predetermined time, and a line range of a reaction curve is estimated on the basis of the second approximation formula, the time required to determine a line range can be shortened. Moreover, inclusion of a function of outputting an index of precision for a line range allows assurance of the precision of a laboratory test value and a predictive value.

BRIEF DESCRIPTION OF DRAWINGS

FIG. 16 is a chart showing an example of a table describing a predicted value, a laboratory test value, and indices of precision.

DESCRIPTION OF EMBODIMENTS

Embodiments of the present invention will be described below with reference to the drawings. Note that the system configuration and details of processing operations (to be described later) are examples for illustrating the invention. The present invention also includes an invention obtained by combining a known technology with the system configuration and processing operation (to be described later) and an invention obtained by replacing part of the system configuration and processing operation (to be described later) with a known technology.

Embodiments

[First Embodiment]

Figure 3:
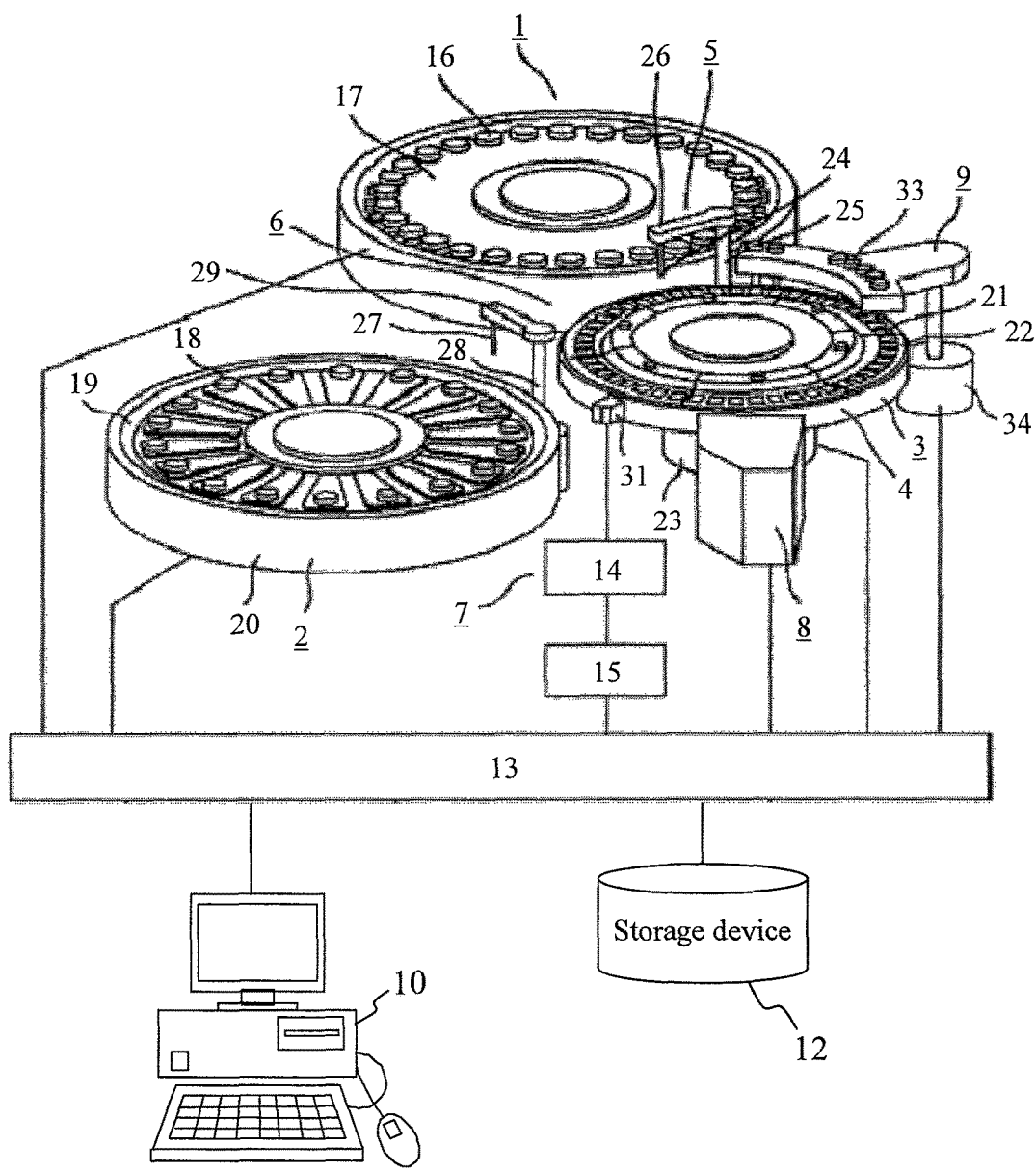
FIG. 3 is a view showing an example of the schematic configuration of an automated analyzer.

The system configuration and processing operation of an automated analyzer according to a first embodiment will be described below in detail with reference to the drawings. FIG. 3 shows the schematic configuration of a biochemical automated analyzer equipped with an analysis function according to the present invention.

The biochemical automated analyzer includes a sample disc 1, a reagent disc 2, a reaction disc 3, a reaction vessel 4, a sampling mechanism 5, a pipetting mechanism 6, a stirring mechanism 7, a photometry mechanism 8, a washing mechanism 9, a computer (PC) 10, a storage device 12, a control unit 13, a piezoelectric element driver 14, a stirring mechanism controller 15, a specimen container 16, circular discs 17 and 19, a reagent bottle 18, a cooling box 20, a reaction container 21, a reaction container holder 22, a drive mechanism 23, probes 24 and 27, support shafts 25 and 28, arms 26 and 29, a fixation unit 31, a nozzle 33, and a vertical drive mechanism 34. The storage device 12 stores analysis parameters, the number of analyses that can be made using each reagent bottle, the maximum allowable number of analyses, calibration results, analysis results, and the like.

A specimen is analyzed in the biochemical automated analyzer in the order of sampling, reagent dispensation, stirring, photometry, reaction container washing, and data processing such as concentration conversion.

The sample disc 1 is controlled by the control unit 13 via the computer 10. A plurality of specimen containers 16 are circumferentially arranged and set on the sample disc 1. The specimen containers 16 move to below the probe 24 according to analysis order. A sample in each specimen container 16 is dispensed into the corresponding reaction container 21 in a specific amount at a time by a specimen pump which is coupled to the sample sampling mechanism 5.

Each reaction container 21 with the dispensed specimen is moved through the reaction vessel 4 to a first reagent addition position. A reagent sucked from the reagent bottle 18 by a reagent pump (not shown) which is coupled to the reagent dispensation probe 27 is added to the moved reaction container 16 in a specific amount. After the first reagent is added, the reaction container 21 is moved to the position of the stirring mechanism 7, and first stirring is performed. Such an operation of adding and stirring a reagent is performed for each of, for example, first to fourth reagents.

The reaction container 21, in which the contents are stirred, is arranged in a light beam emitted from a light source. A part of the light beam passes through the reaction container 21 while another part of the light beam is absorbed by the contents. The degree of absorption is detected by the photometry mechanism 8 composed of, for example, a multi-wavelength photometer. The photometry mechanism 8 outputs the degrees of absorption related to the sample detected with a lapse of time as measurement point data (absorbance signals) to the control unit 13. The control unit 13 determines a line range of the measurement point data through data processing (to be described later) and then calculates a laboratory test value (the slope of the line range) of the sample. The calculated laboratory test value (data) is stored in the storage device 12 and is displayed on a display device which is attached to the computer 10. The reaction container 21 that has undergone photometry is conveyed to the position of the washing mechanism 9 and washed. After the washing, the reaction container 21 is used for a subsequent analysis.

Figure 1:
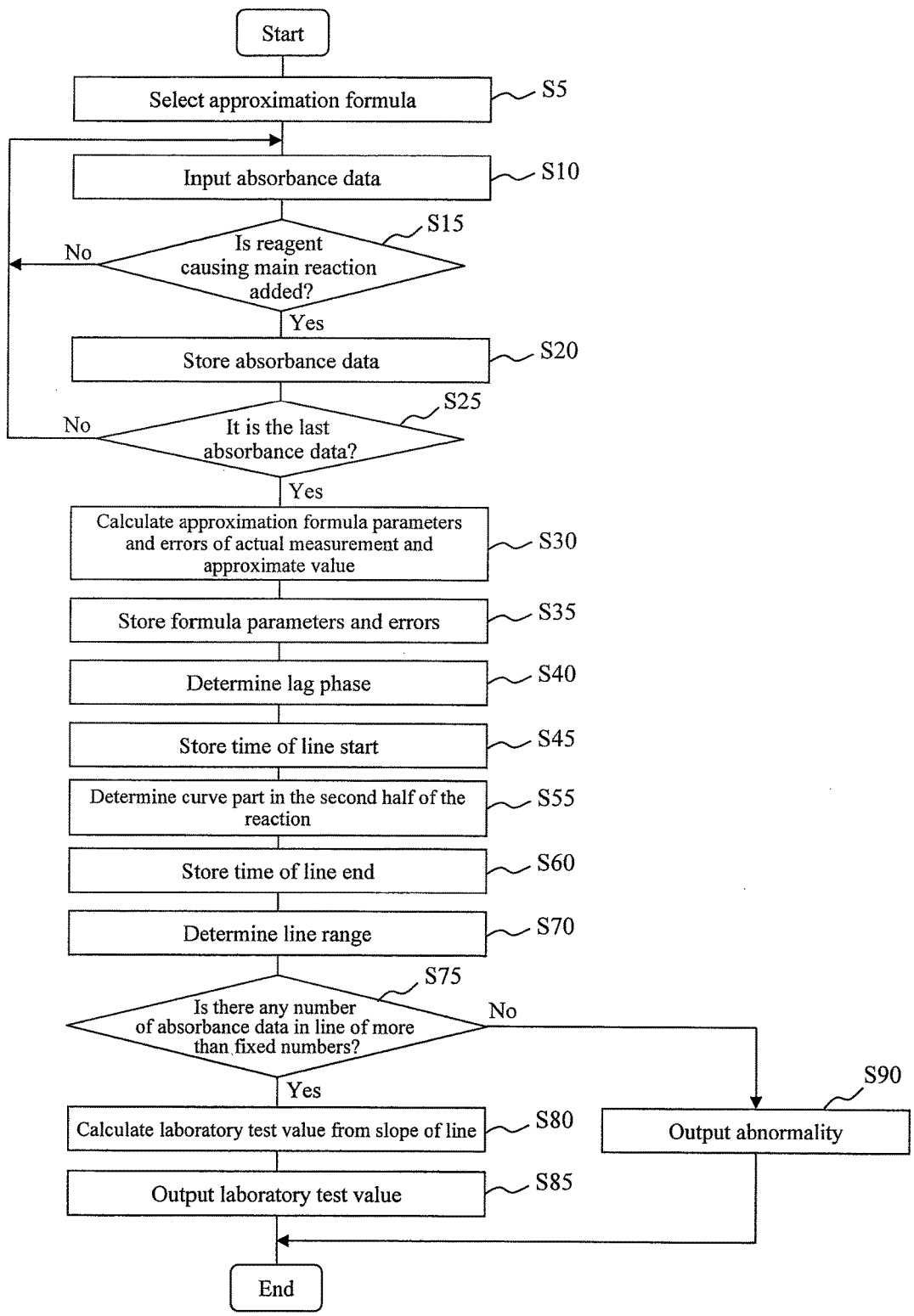
FIG. 1 is a process flow chart according to a first embodiment.
Figure 2:
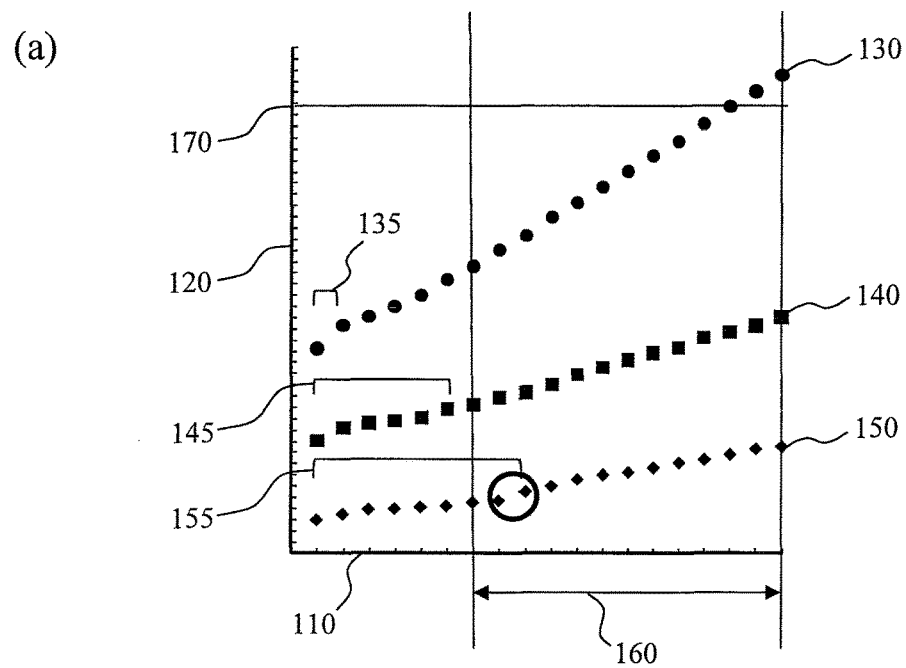
FIG. 2 are graphs for explaining examples of reaction curve data in a rate method.
Figure 2:
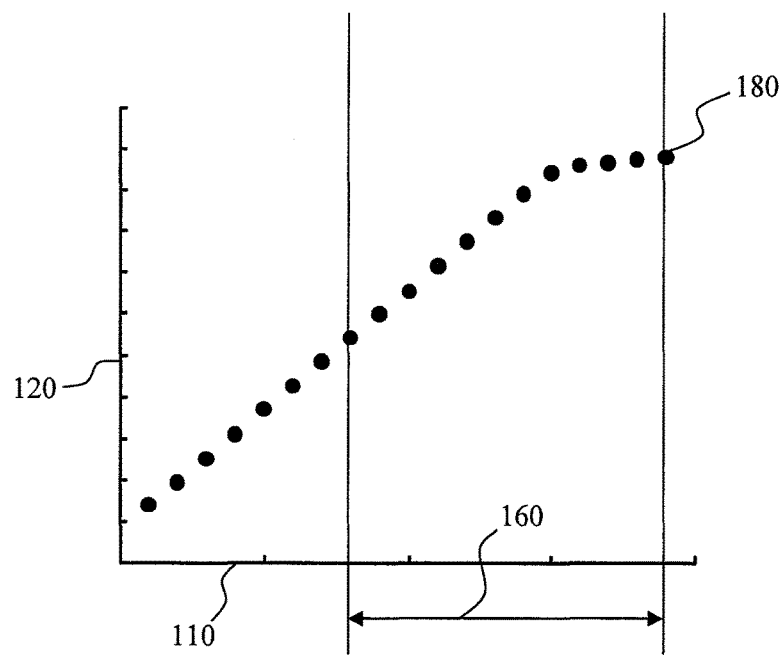
Figure 4:
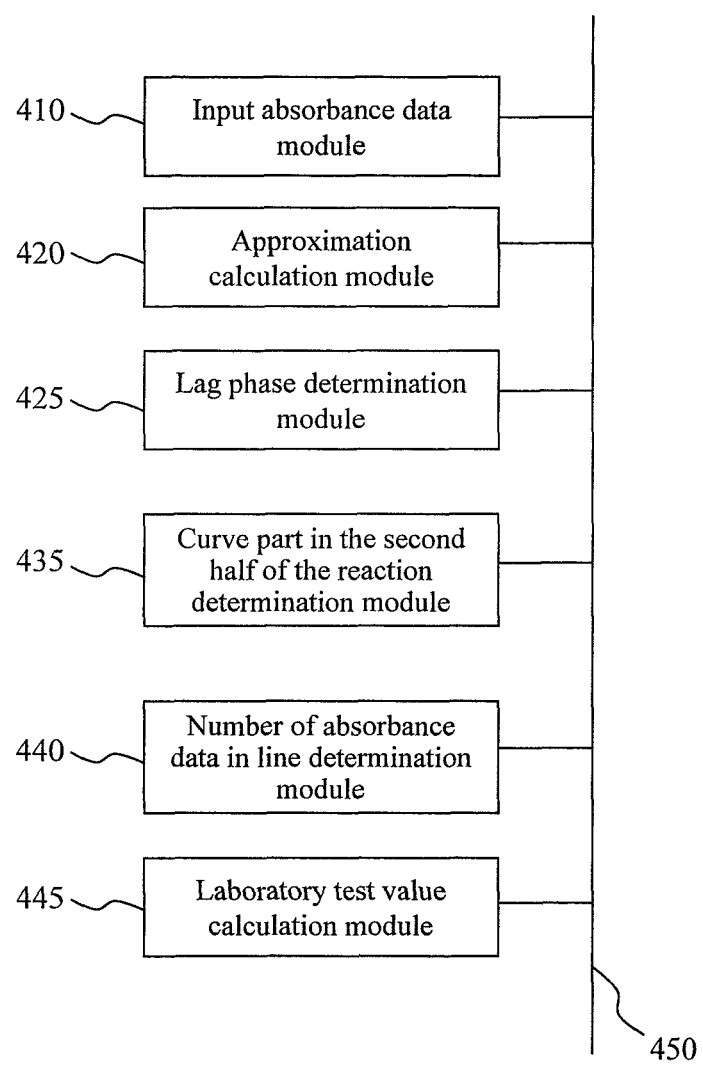
FIG. 4 is a diagram showing an example of the internal configuration of a control unit.

A line range determination procedure to be executed by the control unit 13 will be described. The procedure is shown in FIG. 1. Note that FIG. 1 shows only a part related to a line range determination program to be executed in the control unit 13. FIG. 4 shows functional blocks of the control unit 13 to be implemented through the line range determination program. Note that the determination program is expressed in terms of hardware in FIG. 4. The control unit 13 shown in FIG. 4 is composed of an input absorbance data module 410, an approximation calculation module 420, a lag phase determination module 425, a curve part in the second half of the reaction determination module 435, a number of absorbance data in line determination module 440, a laboratory test value calculation module 445, and a data bus 450 which connects the modules to each other. The modules can mutually pass data via the data bus 450. Note that the functional blocks constituting the control unit 13 may be composed of a piece of hardware other than the control unit 13 or a CPU. The functional blocks constituting the control unit 13, of course, may be implemented as software modules within a single CPU.

First, measurement of an examination item is started for a sample. At the same time as the start of the measurement, in step S5, the approximation calculation module 420 selects an approximation formula (first approximation formula) suitable for line range determination. Assume that a plurality of approximation formulas representing change in absorbance with time as choices are stored in advance in the storage device 12. The approximation calculation module 420 selectively reads out an optimum one corresponding to a combination of the examination item and a reagent from among the plurality of approximation formulas.

In this embodiment, the functions indicated by (Expression 2) to (Expression 5) are the selectable approximation formulas. Note that t and x represent a time and absorbance, respectively, in each function and that a, b, c, d, e, k, p, q, r, u, v, and w are parameters.

$$x = a*t + b + c*\exp(-k*t) \quad \text{(Expression 2)}$$

$$x = a*t + b + e/(t+d) \quad \text{(Expression 3)}$$

$$x = a*t + b + w/\{\exp(u*t) + v\} \quad \text{(Expression 4)}$$

$$x = a*t + b + p*\log\{1 + q*\exp(r*t)\} \quad \text{(Expression 5)}$$

The four given functions are each composed of a component proportional to time, a constant component, and a non-linear component with a different rate of change with time. It is, of course, possible to prepare functions other than the functions as approximation formulas.

Figures 5, 6:
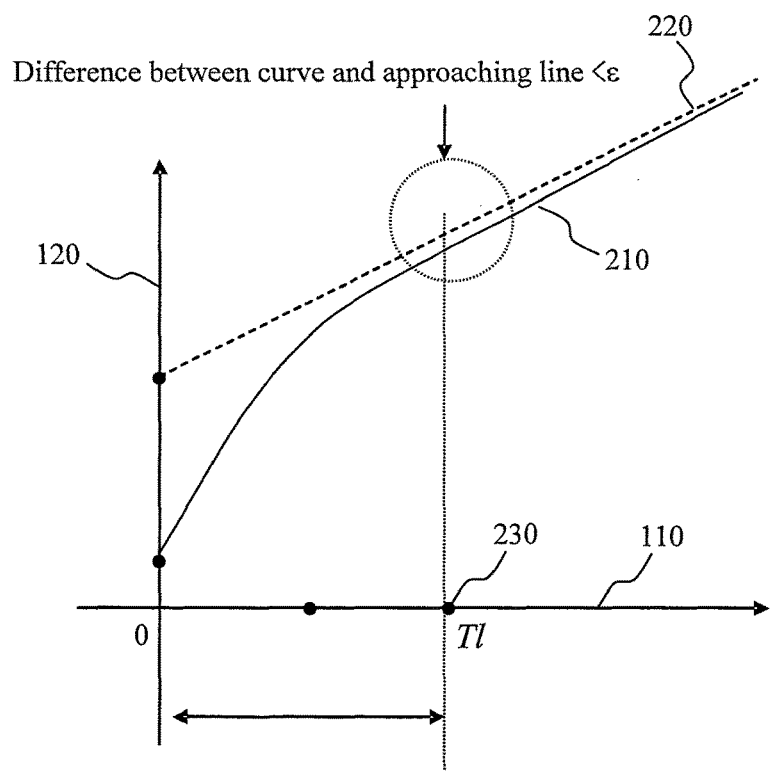
FIG. 5 is a chart showing an example of a table describing the relationship among an examination item, the type of a reagent, and an optimum approximation formula.
FIG. 6 is a graph for explaining a method for digitizing a lag phase.

Note that the approximation formula selection by the approximation calculation module 420 may be performed by automatic execution based on the combination of the examination item and the reagent or by a user's free selection. To implement the former function, for example, optimum approximation formulas may be stored as a table in the storage device 12 for respective combinations of examination items and reagents. The approximation calculation module 420 searches the table by a combination of an examination item and a reagent and selects an optimum approximation formula corresponding to the combination. FIG. 5 shows an example of such a table. A table 500 is composed of columns 510, 520, and 530. The column 510 describes an examination item, the column 520 describes the type of a reagent, and the column 530 describes the type of an optimum approximation formula associated with the examination item and the type of the reagent.

In this embodiment, the approximation calculation module 420 searches the table 500 on the basis of the combination of the examination item and the reagent and selects an approximation formula optimum for line range determination. Note that the configuration may be such that a correspondence stored in the table 500 can be changed by a user.

The absorbance is measured a plurality of times with a lapse of time. In the next step S10, the input absorbance data module 410 inputs absorbance data obtained by one measurement or average absorbance data obtained by a plurality of measurements from the photometry mechanism 8. That is, the absorbance data is input to the control unit 13. In a measurement system using light with two wavelengths, light of a wavelength (main wavelength) in which the absorbance changes significantly in response to a change in color tone associated with reaction between the reagent and the sample and light of a wavelength (sub-wavelength) in which the absorbance changes little, the difference between the absorbance of the main wavelength light and the absorbance of the sub-wavelength light is input as absorbance data.

In step S15, the input absorbance data module 410 determines whether a main reaction reagent is added. If it is determined that the main reaction reagent is not added, the current process returns to step S10 to input next absorbance data. The determination operation is repeatedly executed until it is determined that the main reaction reagent is added. The main reaction agent here refers to a reagent (typically, a final reagent) causing a major change in absorbance in a reaction using a plurality of reagents. If the main reaction agent is added, the current process shifts to step S20.

In step S20, the input absorbance data module 410 stores the input absorbance data in the storage device 12.

In step S25, the input absorbance data module 410 determines whether the last absorbance data is stored. That is, this embodiment requires that all absorbance data corresponding to a predetermined reaction period are stored in the storage device 12 before line range determination. If it is determined that the last absorbance data is not stored in the storage device 12, the current process returns to step S10. The loop operation (absorbance data input and storage) is repeatedly executed until a required number of data are stored in the storage device 12. If the input absorbance data module 410 determines that the required number of data is accumulated, the current process advances to step S30.

In step S30, the approximation calculation module 420 calculates the values of parameters in the approximation formula (first approximation formula) selected in step S5 so as to minimize the difference between a change in absorbance with time represented by the expression and an actual change in absorbance with time. More specifically, the parameter values in the expression are calculated so as to minimize the square error between each absorbance data stored as a measurement result and absorbance data at a corresponding time calculated by the approximation formula. At this time, the last term of each approximation formula (the non-linear component behind (a*t+b) in (Expression 2) to (Expression 5)) is controlled such that parameter values approach "0" with an increase in the time t. Additionally, initial values of parameters in the last term of each approximation formula are set such that the approximation formula fits absorbance data at an early stage of a reaction.

An existing least squares calculation method can be used to calculate the parameter values. As a method supporting expressions in various forms, there is also available a process of calculating the parameter values that minimize the square error by a steepest descent method. In this specification, an approximation formula obtained by optimizing the parameter values of the terms according to each measurement result (each absorbance data) is called a second approximation formula and is distinguished from the first approximation formula selected according to the combination of the examination item and the reagent.

In step S30, the approximation calculation module 420 further calculates for each time the difference (error) between absorbance (an approximate value) calculated by the second approximation formula and actually measured absorbance (an actual measurement).

In step S35, the approximation calculation module 420 stores the parameter values defining the second approximation formula and the difference (error) between the actual measurement and the approximate value calculated for each time in the storage device 12.

In the next step S40, the lag phase determination module 425 calculates a lag phase at an early stage of the reaction where the absorbance changes in a curved manner on the basis of the second approximation formula. FIG. 6 illustrates a method for determining a lag phase.

In FIG. 6, a horizontal axis 110 indicates a time elapsed since the start of a reaction while a vertical axis 120 indicates absorbance. A curve 210 indicates an approximated curve of a change in absorbance obtained from the second approximation formulas. A straight line 220 is a straight line which is approached by the curve 210. A point 230 on the horizontal axis 110 indicates a time (T1) when the curve 210 sufficiently approaches the straight line 220, and the range from 0 to T1 of the horizontal axis 110 corresponds to a lag phase. A time when the lag phase ends corresponds to a start time of line, and a time corresponding to the point 230 is the start time of line.

The time when the curve 210 has sufficiently approached the straight line 220 is defined as, for example, a time when the difference between the curve 210 and the straight line 220 has fallen below a minute value ε that is set in advance. The value ε may be a fixed value or may be set according to initial absorbance or the range of change in absorbance. For example, ε may be set to a value obtained by multiplying the initial absorbance by a constant or a value obtained by multiplying the difference between the initial absorbance and final absorbance by a constant. Alternatively, the sufficiently approached time may be defined as a time when the difference in slope between the curve 210 and the straight line 220 has fallen below a minute value δ that is set in advance. In this case, the value δ may be a fixed value or may be set according to the slope of the straight line 220. For example, δ may be set to a value obtained by multiplying the slope of the straight line 220 by a constant.

In step S45, the lag phase determination module 425 stores a calculated time as the start time of line in the storage device 12.

In the next step S55, the curve part in the second half of the reaction determination module 435 determines a curve part (hereinafter referred to as a "second-half curve part") appearing in a second half of reaction curve data. A method for determining a second-half curve part will be described with reference to FIGS. 7 and 8.

Figure 7:
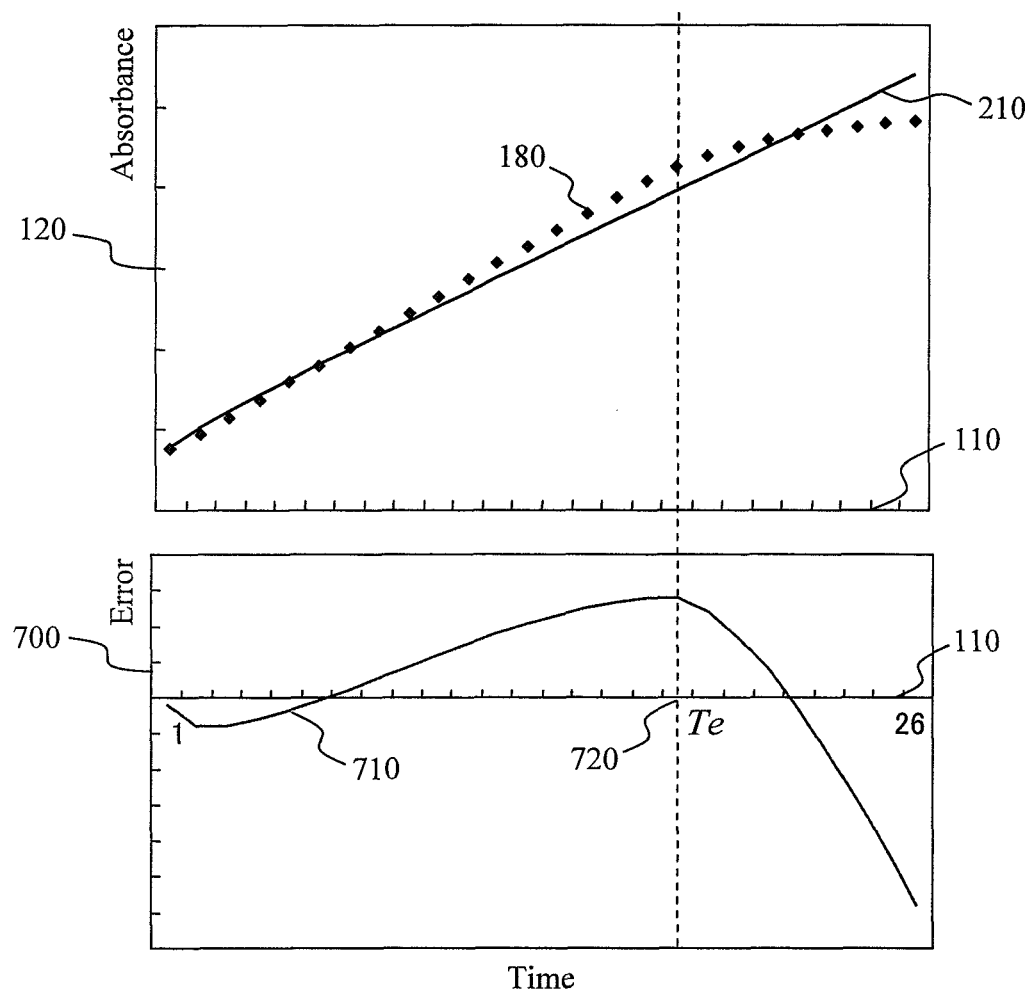
FIG. 7 is a chart for explaining a method for digitizing a curve part in a second stage of a reaction.

The horizontal axis 110 of the upper graph in FIG. 7 represents a time elapsed since the start of a reaction while the vertical axis 120 indicates absorbance. The curve 210 is an approximated curve of a change in absorbance obtained from the second approximation formulas. Reference numeral 180 denotes absorbance data of a sample. The horizontal axis 110 of the lower graph in FIG. 7 represents a time elapsed since the start of the reaction while a vertical axis 700 indicates an error. The error here is given as the difference value between an actual measurement and an approximate value. For example, a curve 710 indicates a change in a value obtained by subtracting an approximate value from an actual measurement with time. If reaction curve data forms a downward curve, an error is obtained as, for example, a value obtained by subtracting an actual measurement from an approximate value. Even in this case, a graph like the lower graph shown in FIG. 7 is obtained.

Since the approximation formulas (Expression 2) to (Expression 5) do not include an expression representing a second-half curve part, if the absorbance data denoted by reference numeral 180 has a curve in a second half, the approximated curve 210 intersects with a reaction curve denoted by reference numeral 180, as indicated by the upper graph in FIG. 7. Accordingly, if a change in the difference (error) between an approximate value and an actual measurement with time is graphically represented, as shown in the lower graph in FIG. 7, the error shows a maximum at a time when the curve starts. In this embodiment, the time is referred to as an end time of line.

Figures 8, 9:
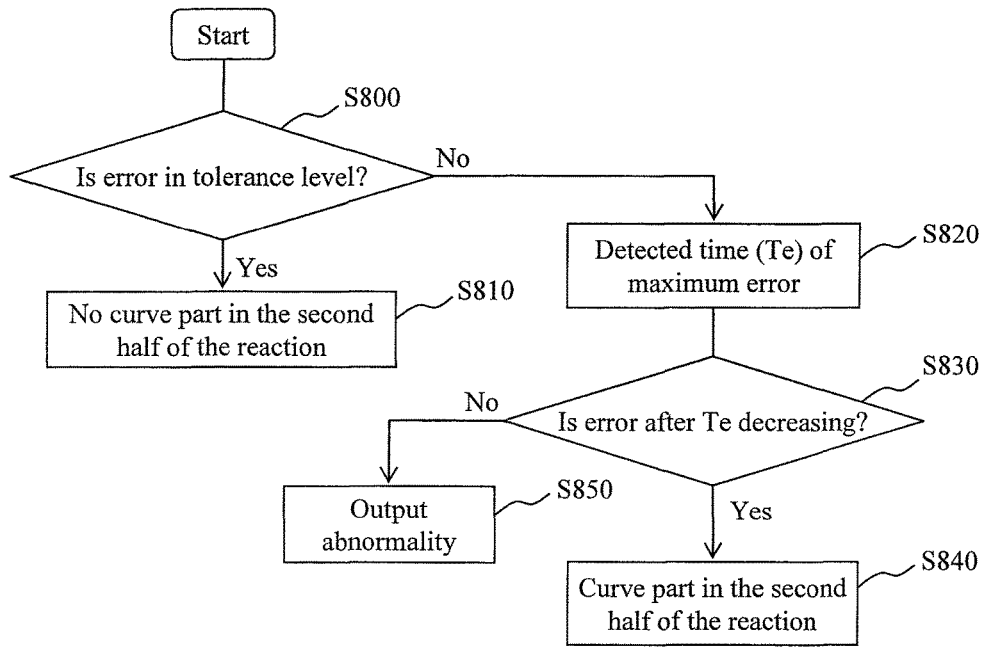
FIG. 8 is a process flow chart for determining a curve part in a second stage of a reaction.
FIG. 9 is a chart showing an example of a table describing the relationship between a sample and a laboratory test value.

A processing operation to be executed by the curve part in the second half of the reaction determination module 435 will be described with reference to FIG. 8. First, in step S800, the curve part in the second half of the reaction determination module 435 reads out the errors stored in the storage device 12 and determines whether the errors are within a predetermined tolerance level. Assume that the tolerance level used for determination is stored in advance in the storage device 12.

If the errors are outside the tolerance level, the curve part in the second half of the reaction determination module 435 advances to step S810. In step S810, the curve part in the second half of the reaction determination module 435 determines that reaction curve data has no curve part in a second half. In this case, an end time of line is equal to a time when the reaction ends. If it is determined in step S800 that any error is outside the tolerance level, the curve part in the second half of the reaction determination module 435 advances to step S820.

In step S820, the curve part in the second half of the reaction determination module 435 monitors a change in error with time as shown in the lower graph in FIG. 7 and detects a time 720 (Te) when the error shows a maximum value.

In the next step S830, the curve part in the second half of the reaction determination module 435 determines whether the distribution of errors after the time 720 exhibits a monotonic decrease. Whether the distribution exhibits a monotonic decrease can be determined on the basis of, for example, whether the sign of the difference between errors at adjacent times is constant. The distribution exhibiting a monotonic decrease indicates that the reaction curve data has a curve part in the second half, as shown in the upper graph in FIG. 7. Accordingly, the curve part in the second half of the reaction determination module 435 advances to step S840 to determine that the reaction curve data has a curve part in the second half. In this case, the end time of line is equal to a time when a curve starts, i.e., the time 720 in FIG. 7. If it is determined in step S830 that the distribution does not exhibit a monotonic decrease, the curve part in the second half of the reaction determination module 435 advances to step S850 to output a signal indicating "abnormality" of measurement. Methods for outputting a signal indicating "abnormality" include a process of issuing an alarm and a process of displaying an alarm on the display device attached to the computer 10 in FIG. 3.

Referring back to FIG. 1, when the processing in step S55 ends, the curve part in the second half of the reaction determination module 435 advances to step S60. In step S60, the curve part in the second half of the reaction determination module 435 stores the end time of line obtained as a determination result in the storage device 12.

In step S70, the number of absorbance data in line determination module 440 determines a line range from the start time of line and the end time of line stored in the storage device 12.

In the subsequent step S75, the number of absorbance data in line determination module 440 determines whether the number of absorbance data appearing within the line range is not less than a predetermined threshold value. Note that a linear function is represented by, for example, a linear expression as indicated by (Expression 6). The number of absorbance data required to obtain the slope of a straight line using (Expression 6) is not less than two. Note that t represents a time, x represents absorbance, and that a and b represent parameters in (Expression 6).

$$x=a*t+b \qquad \text{(Expression 6)}$$

Alternatively, the minimum number of absorbance data required to calculate a reliable laboratory test value may be set in advance from experiment.

If it is determined in the determination processing in step S75 that the number of absorbance data in line is smaller than the threshold value, the number of absorbance data in line determination module 440 advances to step S90 to determine that the measurement has "abnormality." Methods for outputting a signal indicating "abnormality" include a process of issuing an alarm and a process of displaying an alarm on the display device attached to the computer 10 in FIG. 3.

On the other hand, if it is determined in the determination processing in step S75 that the number of absorbance data in line is not less than the threshold value, the number of absorbance data in line determination module 440 advances the current process to step S80. In step S80, the laboratory test value calculation module 445 calculates a linear function approximating the absorbance data within the line range and calculates a slope used for laboratory test value conversion from the linear function.

The linear function calculation (corresponding to the process of calculating a slope) utilizes, for example, an existing least squares calculation method. The laboratory test value calculation module 445 calculates a straight line given by (Expression 6) approximating the absorbance data within the line range, i.e., the slope of the straight line. The laboratory test value calculation module 445 can also calculate a laboratory test value from the slope on the basis of a calibration curve. Calibration curve data is stored in advance in the storage device 12. The line range, for which the linear function is calculated, linear function parameters, and the calculated laboratory test value are stored in the storage device 12.

In the next step S85, the laboratory test value calculation module 445 outputs the calculated laboratory test value. Methods for outputting the laboratory test value include a process of displaying the laboratory test value on the display device attached to the computer 10 in FIG. 3. A display example is shown in FIG. 9. A screen displaying measurement results shown in FIG. 9 is composed of columns 900 to 960. The column 900 describes a sample ID, and the column 910 describes a laboratory test value. The column 905 describes an approximation formula (first approximation formula) used to determine a line range. The column 920 describes a start time (straight line disclosure time) of the line range used for laboratory test value conversion. The column 930 describes an end time (end time of line) of the line range used for laboratory test value conversion. The column 940 describes the number of absorbance data appearing within the line range used for laboratory test value conversion. The column 950 and column 960 describe indices of precision, respectively, when the laboratory test value is calculated from the line range used for laboratory test value conversion and the number of absorbance data. An example of the indices of precision to be used is a CV value. The CV value may be set in advance by carrying out an experiment using a sample for which a laboratory test value is known, such as a sample for calibration. In an experiment, a CV value (a value representing variability, such as dispersion or standard deviation) may be calculated for each of various combinations of start times of line and end times of line (the numbers of absorbance data). Another example of the indices of precision to be used is a combination of an average value and variability (e.g., dispersion or standard deviation) of the numbers of absorbance data. The average value and variability of the numbers of absorbance data may be calculated for each item from results obtained from the last measured ordinary (patient) sample, a sample for calibration, and the like. Note that a sample, the number of samples, and a period used for calculation may be freely selected by a user. Generally, the reliability of a detected value increases with an increase in the number of absorbance data within a line range.

Although an example in which the control unit 13 executes the whole of the processing shown in FIG. 1 has been illustrated in the above-described first embodiment, it is also possible to execute the same processing using a processing unit other than the control unit 13. For example, the processing in FIG. 1 can also be executed as a software process to be executed in the computer (PC) 10. Additionally, an internal storage device of the computer (PC) 10 can be used as the storage device 12.

Figure 10:
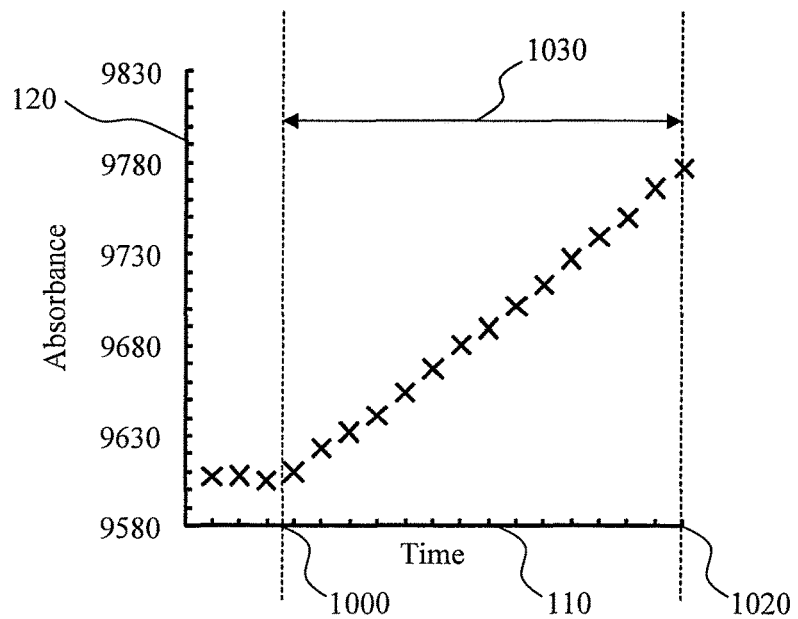
FIG. 10 are graphs for explaining examples of a line range determined using the first embodiment.
Figure 10:
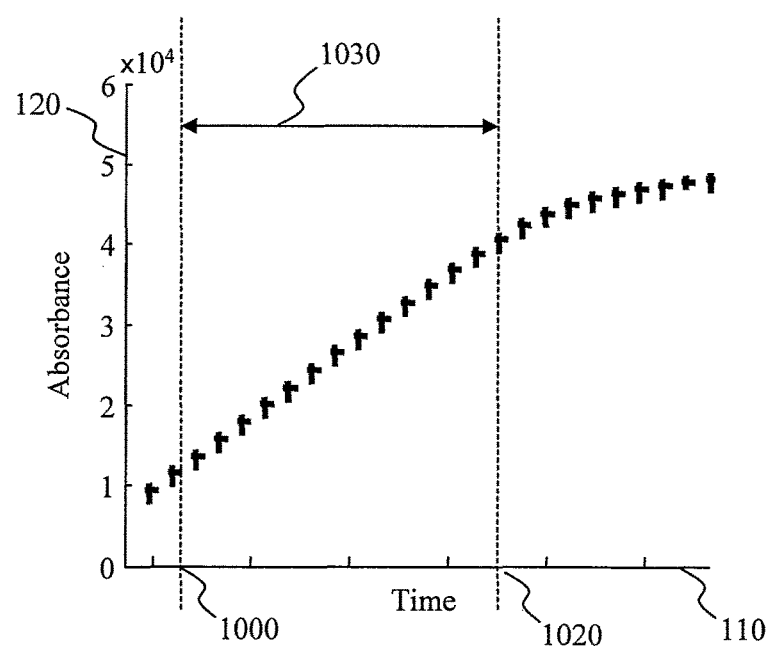

Examples in which a line range is determined according to the first embodiment described above are shown in FIGS. 10(a) and 10(b). The horizontal axis 110 in FIGS. 10(a) and 10(b) indicates a time elapsed since the start of a reaction while the vertical axis 120 indicates absorbance. A time 1000 indicates a start time of line which is determined through the present embodiment, and a time 1020 indicates an end time of line which is determined through the present embodiment. A range 1030 represents a line range which is determined by the present embodiment. Note that FIG. 10(a) shows an example of reaction curve data with a lag phase, and FIG. 10(b) shows an example of reaction curve data with a curve in a second half of a reaction curve. In both cases, it was confirmed that only a linear part not including a curve part could be determined as a line range.

As has been described above, adoption of the line range determination function described in the present embodiment allows determination of a line range used for laboratory test value conversion for each sample. For this reason, a higher-precision laboratory test value can be obtained than by conventional devices, and reexaminations can be reduced. Additionally, since a line range used for laboratory test value conversion, the number of absorbance data, and an index of precision such as a reference CV value or a reference absorbance data average value can be output, the precision of a laboratory test value for each sample can be assured.

[Second Embodiment]

An automated analyzer according to a second embodiment will be described with reference to the drawings. In the present embodiment as well, the automated analyzer is assumed to be a biochemical automated analyzer. Accordingly, the automated analyzer has the same system configuration as that of the first embodiment, i.e., the system configuration shown in FIG. 3. Operations other than the operation of a control unit 13 are the same as those in the first embodiment. A detailed description of the part other than the control unit 13 will thus be omitted.

The processing operation of the control unit 13 will be described below with a focus on a processing operation specific to the present embodiment. In the present embodiment, the control unit 13 determines a line range on the basis of the procedure shown in FIG. 11.

Figure 11:
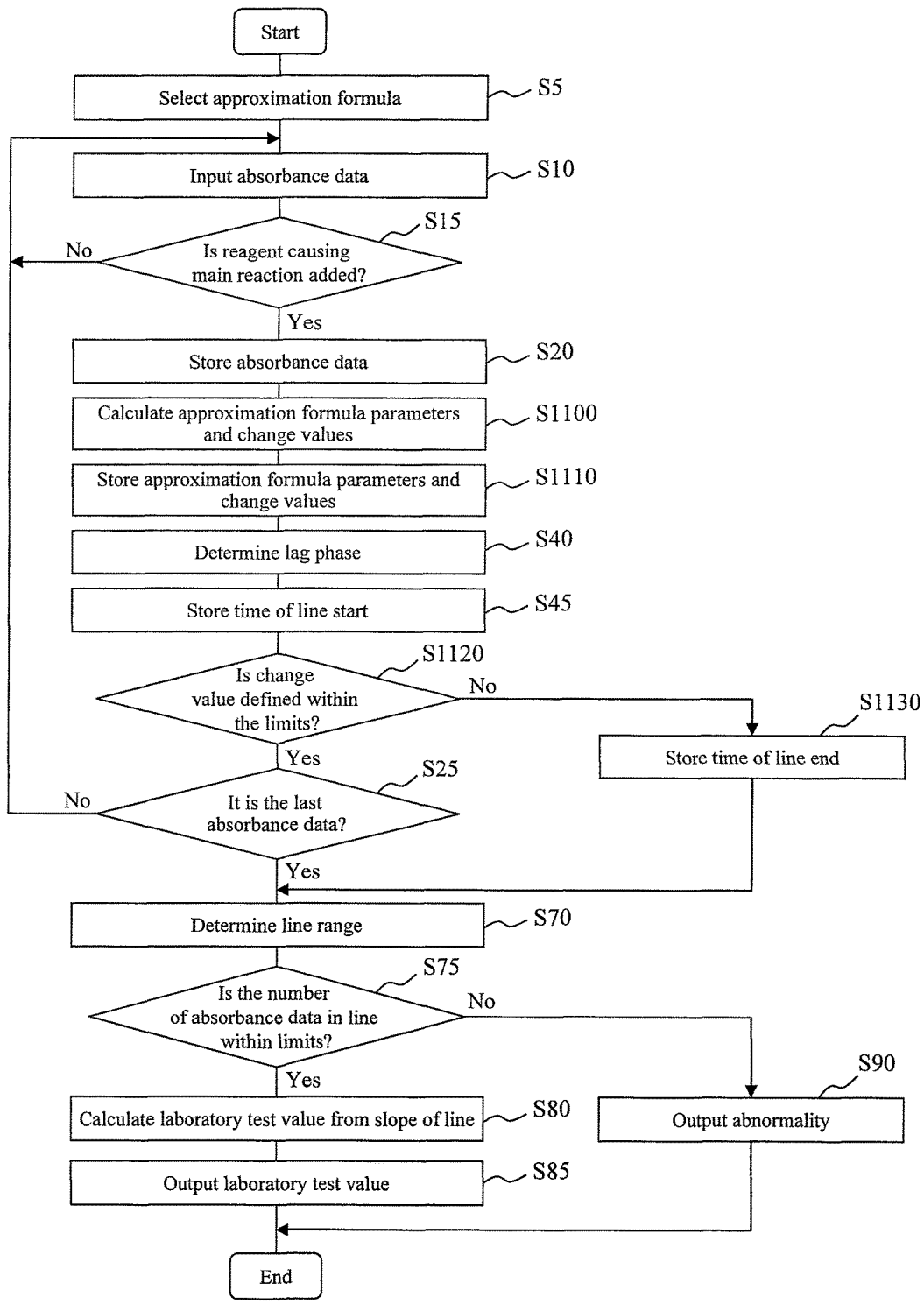
FIG. 11 is a process flow chart according to a second embodiment.

Note that, of the process steps in FIG. 11, ones for performing the same processing as that shown in FIG. 1 are denoted by same reference numerals.

In the second embodiment, the control unit 13 starts a line range start point determination process in parallel with absorbance data measurement operation, without waiting until all absorbance data of a reaction curve are measured.

Of the processes shown in FIG. 11, the processing from step S5 to step S20 is the same as the processing from step S5 to step S20 in FIG. 1.

In the next step S1100, an approximation calculation module 420 calculates approximation formula parameters and change values on the basis of absorbance data acquired thus far. A method for calculating approximation formula parameters is the same as that in step S30 shown in FIG. 1. Note that although a line range is calculated using all acquired absorbance data after acquisition of the last absorbance data in a reaction curve in the first embodiment, approximation formula parameters and a change value are calculated in the second embodiment each time absorbance data is acquired.

The change value here is a value obtained by digitizing a change in an approximation formula parameter with time. To calculate the change value, an approximation formula parameter representing the slope of a linear part is used. For example, if a second approximation formula is given in any one of the forms of (Expression 2) to (Expression 5), the approximation formula parameter a is used. As methods for digitizing a change in a parameter, various methods are available. For example, a process of calculating the difference between a value of a parameter and a value calculated the last time, a process of calculating the fraction of a parameter relative to the parameter calculated the last time, or the like can be used. Note that although attention is focused on only a parameter that gives the slope of a linear part in this embodiment, attention may be focused on, for example, a change in any other parameter such as a parameter of a non-linear part. Alternatively, attention may be focused on changes in parameters of both a linear part and a non-linear part.

In step S1110, the approximation calculation module 420 stores the calculated approximation formula parameters and change values in a storage device 12.

The subsequent step S40 and step S45 are the same as step S40 and step S45 shown in FIG. 1. In this embodiment, a time when the change value falls below a tolerance level is determined as a time when a lag phase ends.

In the next step S1120, a curve part in the second half of the reaction determination module 435 determines whether each calculated change value is within predetermined limits to determine a second-half curve part of reaction curve data. A method for determining a second-half curve part will be described with reference to FIGS. 12 and 13.

Figure 12:
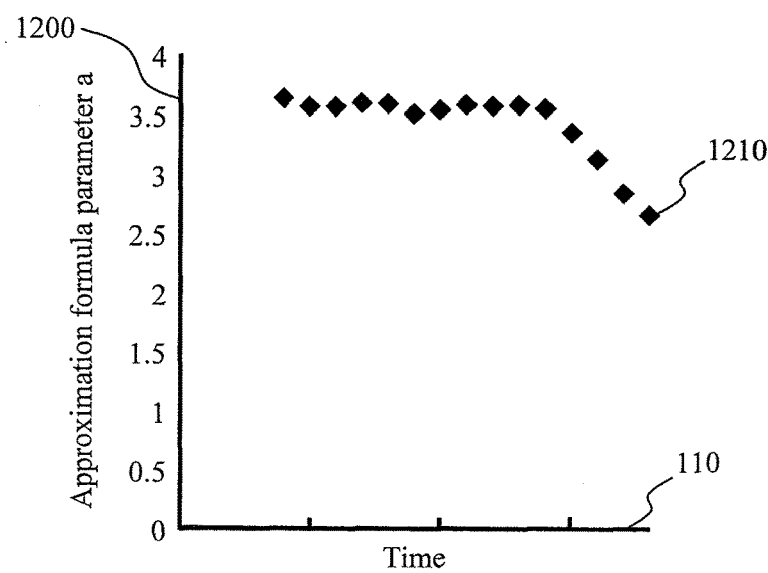
FIG. 12 is a graph showing an example of the distribution of an approximation formula parameter.

FIG. 12 shows a change with time, for example, when the parameter a in (Expression 2) to (Expression 5) is used as the approximation formula parameter representing the slope of a straight line. A horizontal axis 110 indicates a time elapsed since the start of a reaction while a vertical axis 1200 indicates the value of the approximation formula parameter a. Reference numeral 1210 denotes a value of the approximation formula parameter a which is calculated at each time. It can be seen that reaction curve data is located on a straight line while the approximation formula parameter a is substantially constant and that the reaction curve data changes along a curve after the approximation formula parameter a deviates from a constant value.

For example, assume that the approximation formula parameter a is used to calculate the change values. If the approximation formula parameter a is determined to remain constant, the curve part in the second half of the reaction determination module 435 determines the reaction curve data is on a straight line and advances to step S25. On the other hand, if the approximation formula parameter a is determined to have changed, the curve part in the second half of the reaction determination module 435 determines that a line range has ended and advances to step S1130.

Figure 13:
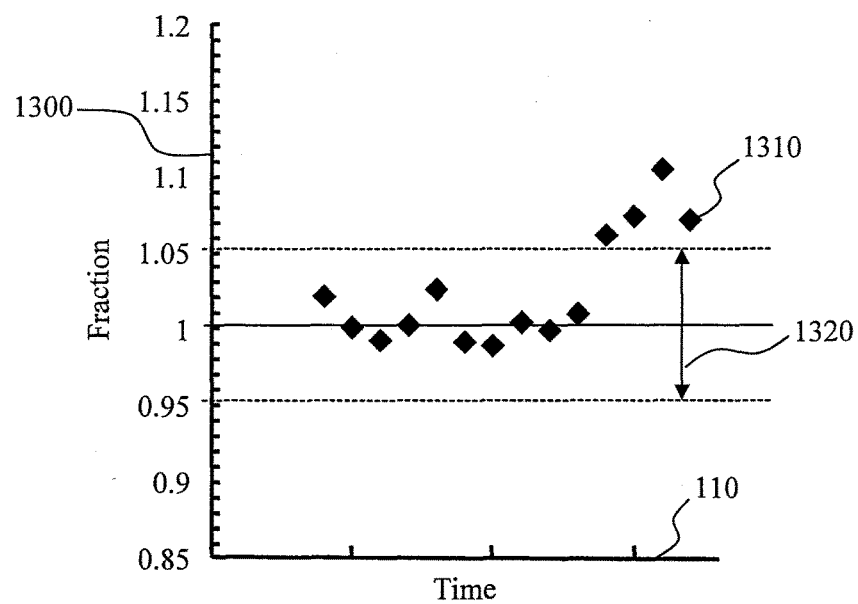
FIG. 13 is a graph showing an example of the distribution of an approximation formula parameter fraction.

FIG. 13 shows a case where the fraction of the parameter relative to the parameter calculated the last time is digitized as a change value on the basis of the distribution of the parameter shown in FIG. 12. The horizontal axis 110 indicates a time elapsed since the start of the reaction while a vertical axis 1300 indicates the parameter fraction. Reference numeral 1310 denotes a value of the fraction of the parameter at each time relative to the parameter calculated the last time. As shown in FIG. 13, the parameter fraction has a value close to 1 if the reaction curve data exhibits linearity and has a value far from 1 if the reaction curve data no longer exhibits linearity.

For example, if the parameter fraction is used as the change value, the curve part in the second half of the reaction determination module 435 reads out a predetermined tolerance level 1320 from the storage device 12 and uses the predetermined tolerance level 1320 for the determination processing in step S 1120. If the parameter fraction is determined to be within the tolerance level, the curve part in the second half of the reaction determination module 435 determines that the reaction curve data is on a straight line and advances to step S25. On the other hand, if the parameter fraction is determined to be outside the tolerance level, the curve part in the second half of the reaction determination module 435 determines that the line range has ended and advances to step S1130.

If the current process advances to step S25, an input absorbance data module 410 determines whether an input absorbance data is the last absorbance data. If it is determined that the absorbance data is not the last absorbance data, the input absorbance data module 410 returns the current process to step S10. On the other hand, if it is determined in step S25 that a required number of data are accumulated, the input absorbance data module 410 advances the current process to step S70.

Note that if the current process has advanced to step S1130, the curve part in the second half of the reaction determination module 435 stores a determined end time of line in the storage device 12 and advances the current process to step S70.

The processing from step S70 to step S90 are the same as the processing from step S70 to step S90 shown in FIG. 1.

Although a case where the same method as that in the first embodiment is used to determine a lag phase (i.e., determine a start time of line) has been illustrated in the above-described second embodiment, it is also possible to use the second-half curve determination method described in step S1120 according to the present embodiment to determine a lag phase. In this case, a time when a change value outside a predetermined tolerance level has changed to fall within the tolerance level may be determined as a start time of line.

Although an example in which the processing shown in FIG. 11 is performed by the control unit 13 has been illustrated in the above-described second embodiment, it is also possible to perform the processing by any other unit of the device. For example, the processing in FIG. 11 can also be executed as software in a computer (PC) 10. Additionally, an internal storage device of the computer (PC) 10 can be used as the storage device 12.

Figure 14:
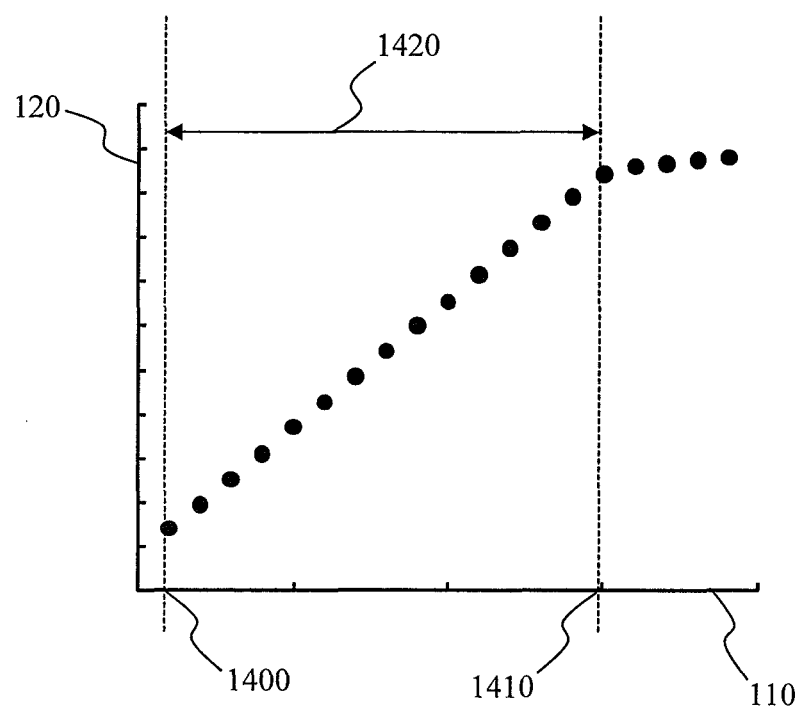
FIG. 14 is a graph for explaining an example of a line range determined using the second embodiment.

FIG. 14 shows an example in which a line range is determined using the processing technique described in the present embodiment. The horizontal axis 110 indicates a time elapsed since the start of a reaction while the vertical axis 120 indicates absorbance. A time 1400 indicates a start time of line which is determined through the present embodiment, and a time 1410 indicates an end time of line which is determined through the present embodiment. A range 1420 indicates a line range which is determined by the present embodiment. As shown in FIG. 14, it was confirmed that only a linear part not including a curve part could be determined as a line range.

As has been described above, use of the second embodiment allows determination of a line range used for laboratory test value conversion for each sample. For this reason, a higher-precision laboratory test value can be obtained than by conventional devices, and reexaminations can be reduced. Additionally, since a second-half curve part can be determined before the last absorbance data is obtained, processing time can be shortened.

Like the first embodiment, since a line range used for laboratory test value conversion, the number of absorbance data, and an index of precision such as a reference CV value or a reference absorbance data average value can be output, the precision of a laboratory test value for each sample can be assured.

[Third Embodiment]

An automated analyzer according to a third embodiment will be described with reference to the drawings. In the present embodiment as well, the automated analyzer is assumed to be a biochemical automated analyzer. Accordingly, the automated analyzer has the same system configuration as that of the first embodiment, i.e., the system configuration shown in FIG. 3. Operations other than the operation of a control unit 13 are the same as those in the first embodiment. A detailed description of the part other than the control unit 13 will thus be omitted.

The processing operation of the control unit 13 will be described below with a focus on a processing operation specific to the present embodiment. In the present embodiment, the control unit 13 determines a line range on the basis of the procedure shown in FIG. 15. Note that, of the process steps in FIG. 15, ones for performing the same processing as that shown in FIG. 1 are denoted by same reference numerals.

In the third embodiment, the feature is that the control unit 13 predictively calculates a laboratory test value before a reaction curve ends (before all absorbance data are measured).

Figure 15:
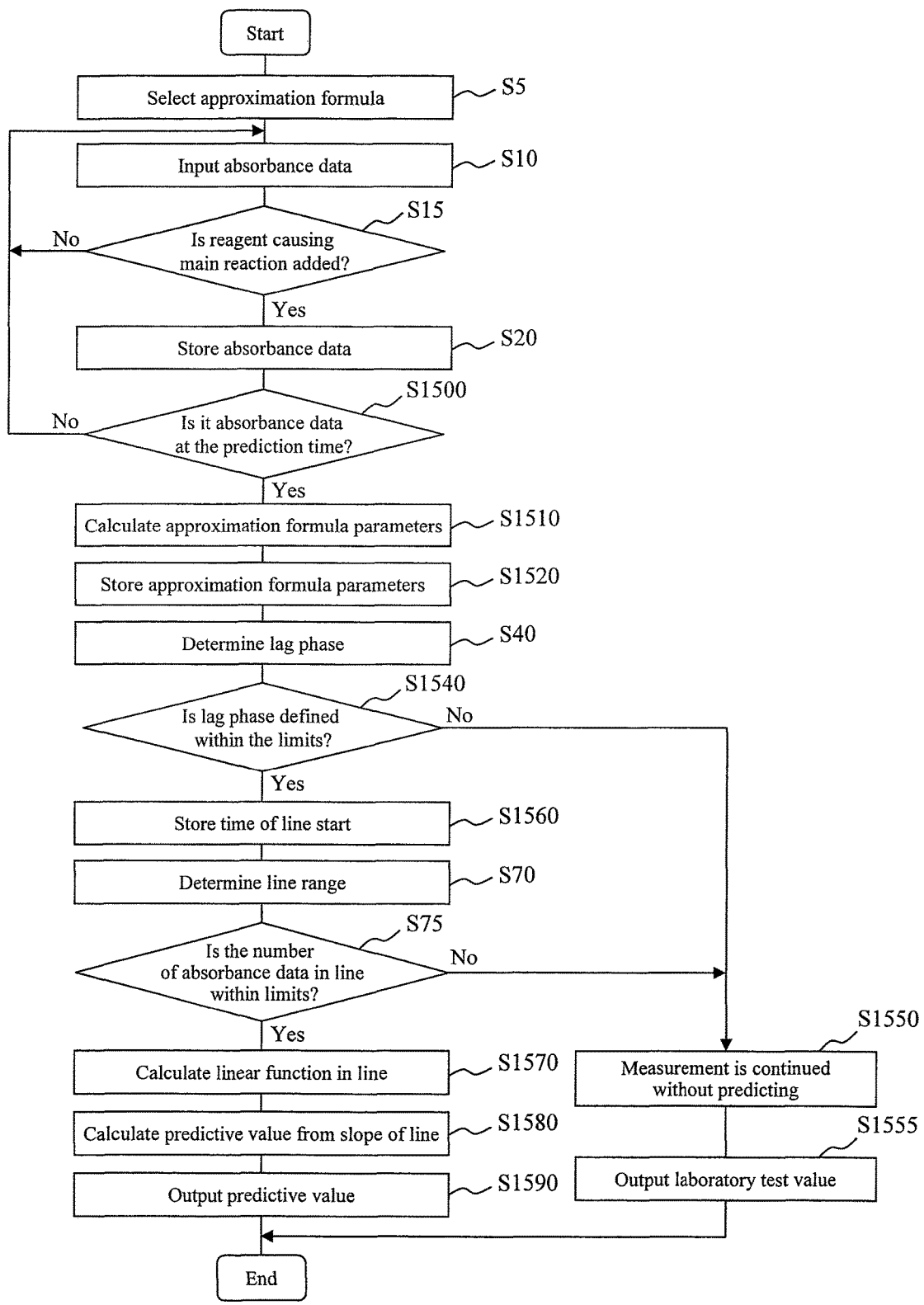
FIG. 15 is a process flow chart according to a third embodiment.

Of the processes shown in FIG. 15, the processing from step S5 to step S20 is the same as the processing from step S5 to step S20 in FIG. 1.

In the next step S1500, an input absorbance data module 410 determines whether absorbance data at a prediction time is stored. The prediction time is a point which is set midway through a reaction curve to calculate a predictive value at a test point (hereinafter referred to as a "predictive detection point.") The prediction time here may be set at one time, regardless of examination item. Alternatively, an optimum prediction time may be set for each examination item. The prediction time is stored in advance in a storage device 12.

If absorbance data at the prediction time is not stored, the input absorbance data module 410 returns the current process to step S10 and repeats absorbance data input and storage until the prediction time is reached. On the other hand, if absorbance data at the prediction time is stored, the input absorbance data module 410 advances to the current process to step S1510.

In step S1510, an approximation calculation module 420 calculates approximation formula parameter values by the same method as that in step S30 of FIG. 1. That is, in the present embodiment, the approximation calculation module 420 calculates second approximation formulas on the basis of only absorbance data which are acquired from the start of a reaction curve to the prediction time.

In the next step S1520, the approximation calculation module 420 stores the calculated approximation formula parameter values in the storage device 12.

The next step S40 is the same as step S40 in FIG. 1. That is, a lag phase determination module 425 calculates a lag phase of reaction curve data on the basis of the calculated second approximation formulas.

In the next step S1540, the lag phase determination module 425 determines whether the length of the calculated lag phase falls within predetermined limits. The process step is executed to determine whether the reaction curve is suitable for detected value prediction. The limits for a lag phase are experimentally set in advance for each item and are stored in advance in the storage device 12. If the determined lag phase is within the predetermined limits, the lag phase determination module 425 advances the current process to step S 1560. On the other hand, if the determined lag phase is outside the predetermined limits, the lag phase determination module 425 advances the current process to step S1550.

If the current process advances to step S 1550, the lag phase determination module 425 stops calculation of a laboratory test value by prediction processing and continues absorbance data accumulation until all absorbance data of the reaction curve are acquired. That is, absorbance data acquisition which has been underway in the background after the prediction time is continued until the whole of the reaction curve ends.

In step S1555 subsequent to step S1550, a laboratory test value of a sample is calculated on the basis of the actual measured data by the same processing technique as those in the first and second embodiment described above and is output.

On the other hand, if the current process advances from step S1540 to step S1560, the lag phase determination module 425 stores an end time of the calculated lag phase, i.e., a start time of line in the storage device 12.

The next step S70 and step S75 are the same as steps S70 and S75 in FIG. 1. Note that the prediction time stored in the storage device 12 is used as an end time of line in step S70. Accordingly, if the start time of line is determined in step S 1560, a line range for the sample is automatically determined.

In step S75, a number of absorbance data in line determination module 440 determines whether the number of absorbance data is within predetermined numerical limits If it is determined in step S75 that the number of absorbance data is outside the predetermined numerical limits, the number of absorbance data in line determination module 440 shifts the current process to step S 1550, i.e., stops prediction processing. On the other hand, if the number of absorbance data is within the limits, the number of absorbance data in line determination module 440 shifts the current process to step S 1570.

In step S1570, a laboratory test value calculation module 445 calculates a linear function approximating the absorbance data within the line range and calculates a slope used for laboratory test value conversion from the linear function. The laboratory test value calculation module 445 calculates parameters of a straight line given by (Expression 6) using, for example, an existing least squares calculation method such that the straight line approximates the absorbance data within the line range, i.e., the slope of the straight line.

In step S1580, the laboratory test value calculation module 445 calculates a predictive value of a laboratory test value from the slope of the approximated line on the basis of a calibration curve. Calibration curve data is read out from the storage device 12. After that, the laboratory test value calculation module 445 stores the line range used to calculate the linear function, the linear function parameters, and the calculated predictive value in the storage device 12.

In the next step S1590, the laboratory test value calculation module 445 outputs the calculated predictive value. Methods for outputting the laboratory test value include a process of displaying the laboratory test value on a display device attached to a computer 10 in FIG. 3. A display example is shown in FIG. 16. A screen displaying measurement results shown in FIG. 16 is composed of columns 900, 905, 910, 920, 930, 940, 950, 960, 1605, 1620, 1630, 1640, 1650, 1660, and 1670. The column 900 describes a sample ID, and the column 905 describes an approximation formula (first approximation formula) used for prediction and laboratory test value output. The column 1605 describes a predictive value, and the column 1620 describes a start time (start time of line) of a straight line used for prediction. The column 1630 describes an end time (end time of line) of the straight line used for prediction, and the column 1640 describes the number of absorbance data in line used for prediction. The column 1650, column 1660, and column 1670 describe indices of precision, respectively, when a predictive value is calculated from the absorbance data in line used for prediction. An example of the indices of precision to be used is a CV value. The CV value may be set in advance by carrying out an experiment using a sample for which a laboratory test value is known, such as a sample for calibration. In an experiment, a CV value (a value representing variability, such as dispersion or standard deviation) when prediction is performed for each of various combinations of start times of line and end times of line (the numbers of absorbance data) may be calculated. Another example of the indices of precision to be used is a combination of an average value and variability (e.g., dispersion or standard deviation) of the numbers of absorbance data. The average value and variability of the numbers of absorbance data may be calculated for each item from prediction results obtained from the last measured ordinary (patient) sample, a sample for calibration, and the like. Note that a sample, the number of samples, and a period used for calculation may be freely selected by a user. Still another example of the indices of precision to be used is a precision rate (concordance rate). The precision rate may be calculated for each item and each number of absorbance data from results as predictive values and laboratory test values obtained from the last measured ordinary sample, a sample for calibration, and the like. Note that a sample, the number of samples, and a period used for calculation may be freely selected by a user.

Note that if the current process advances to step S 1550 in FIG. 15, not a predictive value but a laboratory test value is output. In this case, a result may be described in the columns 910 to 960 in FIG. 16. The columns 910 to 960 are the same as those in the first embodiment, and a detailed description thereof will be omitted.

Although a case where a normal laboratory test value is not output when a predictive value is output has been illustrated in the above-described third embodiment, it is also possible to adopt a system in which prediction and normal measurement are simultaneously performed and a laboratory test value obtained from the normal measurement and a predictive value are both output. The processing described in the first embodiment or the second embodiment may be used for the normal measurement. As an output example in this case, both of the column 1605 to column 1670 related to a predictive value and the column 910 to column 960 related to a laboratory test value may be described, as indicated by the sample ID of 3 in FIG. 16.

Although an example in which the control unit 13 executes the whole of the processing shown in FIG. 15 has been illustrated in the above-described third embodiment, it is also possible to execute the same processing using a processing unit other than the control unit 13. For example, the processing in FIG. 15 can also be executed as software in the computer (PC) 10. Additionally, an internal storage device of the computer (PC) 10 can be used as the storage device 12.

As has been described above, in the third embodiment, since only absorbance data constituting a linear part are used for prediction, the precision of approximation increases, which allows high-precision prediction. Additionally, a line range is determined for each sample, and a predictive value can be output for each sample with higher precision. Moreover, prediction processing does not require waiting for the end of a reaction curve. This allows shortening of the time until a predictive value is output. Furthermore, since a line range used for prediction, the number of absorbance data, and an index of precision such as a reference CV value or a reference precision rate are output, the precision of a predictive value for each sample can be assured.

INDUSTRIAL APPLICABILITY

As has been described in the first and second embodiments, an automated analyzer to which the present invention is applied can provide a high-precision laboratory test value for an examination item measured by a rate method and can contribute to improvement in the reliability of examination. As has been described in the third embodiment, an automated analyzer to which the present invention is applied allows high-precision prediction for an examination item measured by a rate method and can contribute to shortening of examination time.

REFERENCE SIGNS LIST 1 sample disc
2 reagent disc
3 reaction disc
4 reaction vessel
5 sampling mechanism
6 pipetting mechanism
7 stirring mechanism
8 photometry mechanism
9 washing mechanism
10 computer (PC)
12 storage device
13 control unit 14 piezoelectric element driver
15 stirring mechanism controller
16 specimen container
17 circular disc
18 reagent bottle
19 circular disc
20 cooling box
21 reaction container
22 reaction container holder
23 drive mechanism
24 probe
25 support shaft
26 arm
27 probe
28 support shaft
29 arm
31 fixation unit
33 nozzle
34 vertical drive mechanism
110 horizontal axis (lapse of time)
120 vertical axis (absorbance)
130 reference numeral (absorbance at each time)
135 range (lag phase)
140 reference numeral (absorbance at each time)
145 range (lag phase)
150 reference numeral (absorbance at each time)
155 range (lag phase)
160 time range (range used for laboratory test value conversion)
180 reference numeral (absorbance at each time)
210 curve (curve representing absorbance calculated from approximation formula)
220 straight line (straight line approached by curve approximating reaction curve data)
230 point (time when curve 210 approximating reaction curve data has sufficiently approached straight line 220)
410 input absorbance data module
420 approximation calculation module
425 lag phase determination module
435 curve part in the second half of the reaction determination module
440 number of absorbance data in line determination module
445 laboratory test value calculation module
450 data bus
500 table (examination item/reagent/optimum approximation formula)
510 column (examination item)
520 column (type of reagent)
530 column (type of approximation formula)
700 vertical axis (error)
710 curve (curve representing error at each time)
720 time (time indicating maximum error)
900 column (sample ID)
905 column (type of approximation formula)
910 column (laboratory test value)
920 column (start time of line)
930 column (end time of line)
940 column (the number of absorbance data in line)
950 column (first index of precision)
960 column (second index of precision)
1000 time (start time of line)
1020 time (end time of line)
1030 range (line range)
1200 vertical axis (value of approximation formula parameter)
1210 reference numeral (calculated value of approximation formula parameter at each time)
1300 vertical axis (approximation formula parameter fraction)
1310 reference numeral (calculated value of approximation formula parameter fraction at each time)
1320 tolerance level
1400 time (start time of line)
1410 time (end time of line)
1420 range (line range)
1610 column (predictive value)
1620 column (start time of line used for prediction)
1630 column (end time of line used for prediction)
1640 column (the number of absorbance data in line used for prediction)
1650 column (first index of precision)
1660 column (second index of precision)
1670 column (third index of precision)

The invention claimed is:

1. An automated analyzer for mixing a specimen and a reagent and measuring a change in a mixture of the specimen and the reagent with time to reduce a number of reexaminations and shorten a measurement time of the mixture of the specimen and reagent, comprising:
an absorption detection mechanism configured to detect degrees of absorption related to mixing of the specimen and the reagent and to output a reaction curve of the specimen and the reagent based on the detected degrees of absorption;
a measurement point data acquisition unit which acquires a plurality of measurement point data from the reaction curve of the specimen and the reagent;
a data processing unit which processes the measurement point data;
a storage unit which stores a first approximation formula used by the data processing unit;
an output unit which outputs a processing result from the data processing unit; and
a measuring unit that utilizes the processing result to conduct the measuring of the change in the mixture of the specimen and the reagent with a reduced number of reexaminations and a shorten measurement time,
wherein the data processing unit causes the first approximation formula stored in the storage unit, which approaches a straight line to approximate the plurality of measurement point data, calculates a straight line which is approached by second approximation formula that is obtained as a result of the approximation, sets a time when a difference between the straight line and the second approximation formula falls below a reference value or a difference between a slope of the straight line and a slope of the second approximation formula falls below a reference value as a start time of line, and determines a line range of the reaction curve,
wherein the data processing unit calculates the second approximation formula using ones of the plurality of measurement point data which are acquired up to a predetermined time and estimates the line range of the reaction curve on the basis of the second approximation formula to shorten the measurement time thereof,
wherein the data processing unit calculates the straight line which is approached by the second approximation formula, sets a time when a difference between the straight line and the second approximation formula falls below a reference value as a start time of line,
wherein the data processing unit calculates a difference value between each of ones of the measurement point data after the start time of line and the straight line which is approached by the second approximation formula and determines, as an end time of line, a time when the difference value reaches a maximum,
wherein the data processing unit calculates an abnormality as a result of it being determined that a number of absorbance data in line is smaller than the threshold value,
wherein the data processing unit calculates the straight line and calculates a slope used for a laboratory test value conversion from the linear function as a result of it being determined that the number of absorbance data in line is not less than the threshold value to reduce the number of reexaminations,
wherein the data processing unit outputs the calculated laboratory test value on a display screen.

2. The automated analyzer according to claim 1,
wherein the storage unit stores a reference range for the start time of line, and the data processing unit compares the reference range with an estimated value of the line range and determines on the basis of a result of the comparison whether the line range can be estimated.

3. The automated analyzer according to claim 1,
wherein the storage unit stores a reference value of the number of ones of the measurement point data which are to be included in the line range, and
the data processing unit includes a process of counting the number of measurement point data included in the line range that is estimated through signal processing and a process of comparing the reference value with the counted number of measurement point data and determining whether the line range can be estimated.

4. The automated analyzer according to claim 1,
wherein the first approximation formula is one of the following Expressions 1 to 4:

$$x = a^*t + b + c^*\exp(-k^*t) \quad \text{(Expression 1)}$$

$$x = a^*t + b + e/(t+d) \quad \text{(Expression 2)}$$

$$x = a^*t + b + w/\{\exp(u^*t) + v\} \quad \text{(Expression 3)}$$

$$x = a^*t + b + p^*\log\{1 + q^*\exp(r^*t)\} \quad \text{(Expression 4)}$$

where t represents a time, x represents absorbance, and a, b, c, d, e, k, p, q, r, u, v, and w are parameters.

5. The automated analyzer according to claim 1,
wherein the data processing unit calculates a straight line which is approached by the second approximation formula and determines a time when a difference between the straight line and the second approximation formula falls below a reference value as a start time of line.

6. The automated analyzer according to claim 1,
wherein the data processing unit calculates a difference value between each of ones of the measurement point data after the start time of line and the straight line which is approached by the second approximation formula and determines, as an end time of line, a time when the difference value reaches a maximum.

7. The automated analyzer according to claim 1,
wherein the data processing unit includes a process of sequentially calculating the second approximation formula using each of a determining, as the start time of line, a time when a change in at least one parameter of the sequentially calculated second approximation formula falls below a tolerance level.

8. The automated analyzer according to claim 1,
wherein the data processing unit includes a process of sequentially calculating the second approximation formula using each of a plurality of measurement point data which are acquired at respective times even after the start time of line is determined and a process of determining, as an end time of line, a time when a change above a threshold value in at least one parameter of the sequentially calculated second approximation formula is detected.

9. The automated analyzer according to claim 8,
wherein the one parameter is a parameter which gives a slope of a linear component defining the second approximation formula.

10. The automated analyzer according to claim 1,
wherein the storage unit stores a reference value of the number of ones of the measurement point data which are to be included in the line range, and
the data processing unit includes a process of counting the number of measurement point data included in the line range that is determined through signal processing and a process of determining presence or absence of an abnormality related to the line range that is determined by comparing the reference value with the counted number of measurement point data.

11. The automated analyzer according to claim 1,
wherein the data processing unit includes a process of calculating an index of precision for the determined line range and a process of outputting the calculated index of precision to the output unit.

12. An automated analysis method for measuring a change in a mixture of a specimen and a reagent with time using an automated analyzer to reduce a number of reexaminations and shorten a measurement time of the mixture of the specimen and reagent, comprising:
a process of detecting degrees of absorption related to mixing of the specimen and the reagent and generating a reaction curve of the specimen and the reagent based on the detected degrees of absorption;
a process of acquiring a plurality of measurement point data from a reaction curve of the specimen and the reagent by the automated analyzer;
a process of causing a first approximation formula read out from a storage unit which approaches a straight line to approximate the plurality of measurement point data by the automated analyzer; and
a process of calculating a straight line which is approached a second approximation formula that is obtained as a result of the approximation, setting a time when the difference between the straight line and the second approximation formula falls below a reference value or a difference between a slope of the straight line and a slope of the second approximation formula falls below a reference value as a start time of line, and determining a line range of the reaction curve,
a process of measuring that utilizes the processing result to conduct the measuring of the change in the mixture of the specimen and the reagent with a reduced number of reexaminations and a shorten measurement time,
wherein the data processing unit calculates the second approximation formula' using ones of the plurality of measurement point data which are acquired up to a predetermined time and estimates the line range of the reaction curve on the basis of the second approximation formula to shorten the measurement time thereof,
wherein the data processing unit calculates a straight line which is approached by the second approximation formula, sets a time when a difference between the straight line and the second approximation formula falls below a reference value as a start time of line, wherein the data processing unit calculates a difference value between each of ones of the measurement point data after the start time of line and the straight line which is approached by the second approximation formula and determines, as an end time of line, a time when the difference value reaches a maximum, wherein the data processing unit calculates an abnormality as a result of it being determined that the number of absorbance data in line is smaller than the threshold value, wherein the data processing unit calculates the straight line and calculates a slope used for a laboratory test value conversion from the linear function as a result of it being determined that the number of absorbance data in line is not less than the threshold value to reduce the number of reexaminations, wherein the data processing unit outputs the calculated laboratory test value on a display screen.

\* \* \* \* \*